US 6,737,529 B2

(12) United States Patent
Chinaraju et al.

(10) Patent No.: US 6,737,529 B2
(45) Date of Patent: May 18, 2004

(54) PROCESS FOR THE PREPARATION OF 2-CHLORO-5-METHYLPYRIDINE-3-CARBALDEHYDE

(75) Inventors: Bhimapaka Chinaraju, Hyderabad (IN); Vaidya Jayathirtha Rao, Hyderabad (IN); Kondapuram Vijaya Raghavan, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 43 days.

(21) Appl. No.: 10/093,447

(22) Filed: Mar. 7, 2002

(65) Prior Publication Data

US 2003/0176705 A1 Sep. 18, 2003

(51) Int. Cl.$^7$ ............................................. C07D 213/12

(52) U.S. Cl. ........................................................ 546/315
(58) Field of Search .......................................... 546/315

(56) References Cited

U.S. PATENT DOCUMENTS 5,708,180 A * 1/1998 Beck et al. .................. 546/315
6,479,664 B1 * 11/2002 Banda et al. ................ 546/315

* cited by examiner

*Primary Examiner*—Patricia L. Morris
(74) *Attorney, Agent, or Firm*—Abelman, Frayne & Schwab

(57) ABSTRACT

The present invention relates to an improved process for the preparation of 2-chloro-5-methylpyridine-3-carbaldehyde which is a useful intermediate in the preparation of a variety of pharmaceutical and pesticide products.

5 Claims, No Drawings

PROCESS FOR THE PREPARATION OF 2-CHLORO-5-METHYLPYRIDINE-3-CARBALDEHYDE

TITLE OF THE INVENTION

The present invention relates to an improved process for the preparation of 2-chloro-5-methylpyridine-3-carbaldehyde which is a useful intermediate for the preparation of a variety of pharmaceutical and pesticide products. In particular, the present invention pertains to the preparation of 2-chloro-5-methylpyridine-3-carbaldehyde having formula 1 as set forth below.

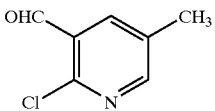

It pertains especially to the preparation of 2-chloro-5-methylpyridine-3-carbaldehyde with a high degree of selectivity.

BACKGROUND OF THE INVENTION

Several pyridine, quinoline, and isoquinoline compounds are important intermediates in that they have been reported as potential anti tumor agents (J.Med.Chem, 19,1209,1976; CA,85:116544q). Carbaldehyde derived products served as ulcer healing agents (Ger. offen DE 3324034,1984; CA,101:54936g), allergy inhibitors (EP 120483,1984; CA,102:95649e; EP120484,1984; CA,102:113500f), antiviral agents (CA,113:172015b), and useful as intermediates for pharmaceuticals (Ger.offen DE 4429465,1996,CA, 124:343116u).

There is only one method disclosed in the literature for the preparation of 2-chloro-5-methylpyridine-3-carbaldehyde in 12% yield. (J. C. S. Perkin. Trans 1,1173, 1984).

The present invention describes an improved process for the preparation of 2-chloro-5-methylpyridine-3-carbaldehyde from N-benzyl-N-(1-Propenyl) acetamide using Vilsemier reagent to achieve a 64% yield, compared to a reported 12% yield.

OBJECT OF THE INVENTION

The main object of the present invention is to provide an improved process for the preparation of 2-chloro-5-methylpyridine-3-carbaldehyde.

Another object of the present invention is to prepare 2-chloro-5-methylpyridine-3-carbaldehyde in higher yields.

SUMMARY OF THE INVENTION

Accordingly the present invention provides an improved process for the preparation of 2-chloro-5-methylpyridine-3-carbaldehyde which comprises reacting N-benzyl-N-(1-Propenyl) acetamide with dimethyl formamide mixed with diphosgene or triphosgene (Vilsmeier) reagent in a molar ratio of N-benzyl-N-(1-Propenyl) acetamide to Vilsmeier reagent in the range of about 0.02:0.35 to about 0.07:0.35, at a temperature in the range of about 0° C. to about 10° C. for about 1 to about 4 hrs, heating the above reaction mixture at a temperature ranging between about 70° C. to about 100° C. for about 4 to about 6 hrs followed by extraction with methylene chloride, and separating the organic layer followed by removal of solvent to obtain the desired product.

In an embodiment of the present invention the molar ratio of N-benzyl-N-(1-Propenyl) acetamide to Vilsemier reagent is preferably about 0.05: 0.35.

In another embodiment the reaction time is preferably 2 hrs.

In yet another embodiment the reaction temperature is preferably in the range of about 75° C. to about 90° C.

In still another embodiment the product yield is 64%.

DETAILED DESCRIPTION

In the improved process for the preparation of the 2-chloro-5-methylpyridine-3-carbaldehyde about 21.93 g (0.3 moles) of dimethylformamide is added to a well stirred and cooled 53.65 g (0.35 moles) of phosphorousoxytrichloride material at a temperature range of about 0° C. to about 20° C. for about 25 to about 35 minutes and then adding to it 9.45 g (0.05 moles) of N-benzyl-N-(1-Propenyl) acetamide at the temperature of about 0 to about 20° C. The above reaction mixture is further continued for 2 hours at a room temperature of about 25° C. The ice cold bath is removed and heated to about 75 to about 90° C. for about 4 to about 6 hours. A orange yellow organic mass is produced which is poured over 200 gms of ice cold water with constant stirring. The mass is then extracted with 2×200 ml of methylene chloride and the layers are separated and then dried over sodium sulfate and the solvent is removed under pressure.

The residue obtained is subjected to chromatographic purification over silicagel to give a 64% yield of 2-chloro-5-methylpyridine-3-carbaldehyde.

The following examples are given by way of illustration of the present invention and therefore should not be construed to the scope of the present invention.

EXAMPLE 1

Dimethylformamide (21.93 g, 0.3 moles) was added to a well stirred and cooled material of phosphorousoxytrichloride(53.65 g, 0.35 moles) at 0° C. in 30 minutes and followed by N-benzyl-N-(1-Propenyl) acetamide (9.45g, 0.05 moles) at the same temperature. The reaction mixture was further continued for 2 hours at room temperature of about 25° C. The ice cold bath was removed and heated to 75° C. for 5 hours. The orange-yellow coloured organic mass was poured to ice cold water (200g) with stirring The mass was extracted with methylenechloride (2×200ml) and the layers were separated. The organic layer was dried over sodium sulfate, and the solvent was removed under reduced pressure. The obtained residue was subjected to chromatographic purification on silicagel to give 2-chloro-5-methylpyridine-3-carbaldehyde in 64% yield.

EXAMPLE 2

Dimethylformamide (21.93 g, 0.3moles) was added to a well stirred and cooled material of phosphorousoxytrichloride (53.65 g, 0.35 moles) at 10° C. in 30 minutes and followed by N-benzyl-N-(1-Propenyl) acetamide (9.45g, 0.05 moles) at the same temperature. The reaction mixture was further continued 2 hours at room temperature of about 25° C. The ice cold bath was removed and heated to 90° C. for 5 hours. The work up procedure was carried out according to the above mentioned procedure. The obtained residue was subjected to chromatographic purification on silica gel to give 2chloro-5-methylpyridine-3-carbaldehyde in 64% yield.

The various advantages attributable to the method of the present invention are as follows:

1. obtaining the highest yield which has ever been reported;
2. employing controlled time and temperature conditions during the reaction, which are critical to the formation of the reagent and the product;
3. avoids the need for any other solvent, reduced reaction times and mild reaction temperatures; and
4. product isolation is extremely simple.

What is claimed is:

1. A process for the preparation of 2-chloro-5-methylpyridine-3carbaldehyde which comprises reacting N-benzyl-N-(1-Propenyl) acetamide with dimethylformamide mixed with diphosgene or triphosgene (Vilsmeier reagent) in a molar ratio of N-benzyl-N-(1-Propenyl) acetamide to Vilsmeier reagent in the range of about 0.02:0.35 to about 0.07:0.35, at a temperature in the range of about 0° C. to about 10° C. for about 1 to about 4 hrs; heating the reaction mixture at a temperature ranging between about 70° C. to about 100° C. for about 4 to about 6 hrs; and, extracting the reaction mixture with methylene chloride and separating the organic layer followed by removal of solvent to obtain the desired product.

2. The process as claimed in claim 1, wherein the mole ratio of N-benzyl-N-(1-Propenyl) acetamide to dimethylformamide mixed with diphosgene or triphosgene (Vilsmeier) reagent is about 0.05:0.35.

3. The process as claimed in claim 1, wherein the reaction time is about 2 hrs.

4. The process as claimed in claim 1, wherein the reaction temperature is in the range of about 75° C. to about 90° C.

5. The process as claimed in claim 1, wherein the product yield is about 64%.

* * * * *